United States Patent
Do et al.

(10) Patent No.: US 11,135,152 B2
(45) Date of Patent: Oct. 5, 2021

(54) NATURAL SHAMPOO COMPOSITION COMPRISING WHITE DANDELION EXTRACT SOLUTION FOR HAIR LOSS PREVENTION AND HAIR GROWTH

(71) Applicants: Jae Nam Do, Geumsan-gun (KR); Pyo Jin Ryu, Sejong-si (KR); Pyo Hyun Ryu, Sejong-si (KR)

(72) Inventors: Jae Nam Do, Geumsan-gun (KR); Pyo Jin Ryu, Sejong-si (KR); Pyo Hyun Ryu, Sejong-si (KR)

( * ) Notice: Subject to any disclaimer, the term of this patent is extended or adjusted under 35 U.S.C. 154(b) by 0 days.

(21) Appl. No.: 16/204,192

(22) Filed: Nov. 29, 2018

(65) Prior Publication Data
US 2020/0170929 A1 Jun. 4, 2020

(51) Int. Cl.
| | | |
|---|---|---|
| *A61K 8/9789* | (2017.01) | |
| *A61Q 7/00* | (2006.01) | |
| *A61Q 5/02* | (2006.01) | |
| A61K 8/67 | (2006.01) | |
| A61K 8/42 | (2006.01) | |
| A61K 8/41 | (2006.01) | |
| A61K 8/64 | (2006.01) | |
| A61K 8/92 | (2006.01) | |
| A61K 8/46 | (2006.01) | |

(52) U.S. Cl.
CPC .............. *A61K 8/9789* (2017.08); *A61Q 5/02* (2013.01); *A61Q 7/00* (2013.01); *A61K 8/416* (2013.01); *A61K 8/42* (2013.01); *A61K 8/466* (2013.01); *A61K 8/64* (2013.01); *A61K 8/673* (2013.01); *A61K 8/678* (2013.01); *A61K 8/922* (2013.01); *A61K 2800/5922* (2013.01); *A61K 2800/805* (2013.01)

(58) Field of Classification Search
None
See application file for complete search history.

(56) References Cited

FOREIGN PATENT DOCUMENTS

| KR | 100581316 | 5/2006 |
|---|---|---|
| KR | 100839704 | 6/2008 |

*Primary Examiner* — Terry A McKelvey
*Assistant Examiner* — Catheryne Chen
(74) *Attorney, Agent, or Firm* — Cantor Colburn LLP

(57) ABSTRACT

Provided is a natural shampoo composition containing a white dandelion extract solution, and more particularly, to a natural shampoo composition containing a white dandelion extract solution, a *Portulaca oleracea* L. extract and a red *Ginseng* which has excellent washing effect and hair loss prevention effect and hair growth promotion effect.

2 Claims, No Drawings

NATURAL SHAMPOO COMPOSITION COMPRISING WHITE DANDELION EXTRACT SOLUTION FOR HAIR LOSS PREVENTION AND HAIR GROWTH

TECHNICAL FIELD

The present invention relates to a natural shampoo composition containing a white dandelion extract solution, and more particularly, a natural shampoo composition having an excellent washing effect, a hair loss prevention effect and a hair-growth promoting effect, including white dandelion extract solution, *Portulaca oleracea* l. extract and red *Ginseng*.

BACKGROUND ART

The average number of human hair is about 80,000-120,0000. Hair has a life-cycle, including periods of development, growth, degeneration, and dormancy, and it is normal to lose about 50-100 strands of hair which enters a dormancy period per day. In the case of the molting animals, all hair strands fall out at the same time and the new strands of hair are produced at the same time because a life cycle of all strands of hair is the same. However, since each strand of hair on the human head has individual hair' life cycle, the human head always maintains a constant number of hairs without molting. Each strand of human hair grows for three years and then falls off again, and after three months, a new strand of hair starts to develop.

However, hair loss may occur due to various stresses and aging effects. In the past, hair loss was attributed to heredity, but in recent years, due to environmental pollution and changes in the living environment, a hair loss has been accelerated. It is known that a hair loss occurs because an energy cycle for hair growth does not function properly and an energy shortage occurs in a hair follicle.

Testosterone, a type of male hormone (androgen), is known to prevent the production of energy needed for hair growth and development. Activity of testosterone increases by the action of 5-alpha reductase distributed around the hair follicle and testosterone changes to DHT (Dihydrotestosterone). Activated DHT binds with the androgen receptor to shorten a growth period of hair and shrink the size of a hair follicle, making the strand of hair thinner and eventually causing hair loss.

Therefore, new drugs are being developed that can prevent hair loss, provided that hair loss would be prevented if male hormones could be controlled. A typical hair loss preventive and hair growth agent includes Propecia™, dutasteride, and minoxidil.

However, when these drugs are used, various side effects are observed, such as sexual dysfunction, allergies, depression, and local inflammation.

Also, compositions for hair loss prevention and hair growth using various natural substances have been proposed. Korean Patent No. 10-0839704 discloses a hair restorer and hair growth promoter composition containing extract of *Chrysanthemum zawadskii* var. *latilobum*. Korean Patent No. 10-0581316 discloses shampoo composition for preventing hair loss and raising hair comprising mixed extract of traditional Chinese medicines.

SUMMARY OF INVENTION

Technical Problem

It is an object of the present invention to provide a natural shampoo composition having an excel lent washing effect, a hair loss prevention effect and a hair-growth promoting effect, including white dandelion extract solution, *Portulaca oleracea* l. extract and red *Ginseng*. The shampoo composition of the present invention is a natural shampoo composition that does not contain a chemical surfactant.

Solution to Problem

The object of the present invention can be achieved by a hair loss preventive and hair-growth shampoo composition comprising, as an active ingredient, 30-50 wt % of white dandelion extract solution, 1-10 wt % of *Portulaca olaracea* L. extract and 1-5 wt % of red *Ginseng*, based on the total weight of the shampoo composition.

According to one embodiment of the present invention, the shampoo composition further comprises at least 10 substances selected from the group consisting of polyquaternium, disodium laureth fosuccinate (LES) cocamide diethanol amine (CDA), cocobetaine, olive liquid, silk amino acid, peptide, glycerin, betaine, panthenol, provitamin E, phyto PS, and essential oil.

According to one embodiment of the present invention, the white dandelion extract solution is prepared by heating a mixed solution of white dandelion and water at 180-100° C.; cooling the mixture to 60-40° C.; adding cinnamon to the cooled mixed solution and again heating the mixed solution at 80-100° C.; and then re-cooling the heated solution. The obtained white dandelion extract solution can be a hot-water extract of white dandelion and cinnamon.

Advantageous Effects

The shampoo composition of the present invention has effects of preventing hair loss and promoting hair-growth while being little irritating, excellent in safety even when used for a long period of time, and having excel lent cleaning effect.

MODE FOR INVENTION

The natural shampoo composition of the present invention contains white dandelion extract solution, *Portulaca oleracea* L. extract and red *Ginseng* as active ingredients. Preferably, the composition contains 30-50 wt % of white dandelion extract, 1-10 wt % of *Portulaca oleracea* L. extract, and 1-5 wt % of red *Ginseng*, based on the total weight of the shampoo composition.

In the present invention, the white dandelion extract solution may be prepared by a solvent extraction method using a solvent such as ethanol, a hot water extraction method using a hot water, a supercritical extraction method, an ultrasonic extraction method, or the like, and may prepared by a hot water extraction method. Hereinafter, a production process of a white dandelion extract solution will be described in detail.

First, the whole plant of white dandelion is washed, then dried and cut. A purified water which is as much as 5-10 times of dry weight of white dandelion is added to the cut whole plant and heated to 80-100° C. When the temperature reaches 100° C., a heat source is removed and the heated solution is naturally cooled down to a room temperature. This is to ensure that active ingredients of white dandelion may be slowly eluted. Cinnamon is added when the temperature of the solution reaches 60-40° C. The cinnamon may be in the form of a dried bark.

Preferably, the weight ratio of white dandelion dry weight to cinnamon is 10:1-3. Cinnamon acts as a natural preservative in the composition, eliminates Demodex folliculorum, and alleviates itching. When the content of cinnamon is less than the above-mentioned weight ratio, it is difficult to exhibit the above effects, and when the weight ratio is exceeded, stimulation may be given to the scalp.

The solution to which cinnamon is added is reheated to 80-100° C. When the temperature reaches 100° C. a heat source is removed and the heated solution naturally is cooled to a room temperature. This is to ensure that active ingredients may be slowly eluted. When the temperature of the solution reaches 40 to 20° C., the solution is filtered using a filter cloth or the like to remove solid contents, and a white dandelion extract solution is prepared. The filtration method may be any known method and is not particularly limited. The white dandelion extract solution as prepared is excellent in antibacterial and sterilizing activities, may eliminate Demodex folliculorum, improve a scalp itching, a blood circulation, a scalp and hair condition, and prevent a hair loss.

*Portulaca oleracea* L. is an annual which grows naturally in Korea, is approximately 3 cm tall, with leaves being 1.5-2.5 cm length and 0.5-1.5 cm width, and blooms in June-September. *Portulaca oleracea* L. is known to be effective in alleviating atopy, eczema, athlete's foot, inflammation and the like and is known to be rich in tannins, saponin, beta-carotene potassium, vitamin C, D and E, omega-3 and the like.

The *Portulaca oleracea* L. extract according to the present invention may be a hot-water extract, a solvent extract using a solvent such as ethanol, or a fermented extract fermented with a microorganism. Preferably it is a hot-water extract.

*Portulaca oleracea* L. hot-water extract will be prepared as follows: a purified water which is as much as 5-10 times of dry weight of white dandelion is added to a washed and dried whole plant of *Portulaca oleracea* L. and then heated to 80-100° C. When the temperature reaches 100° C., a heat source is removed and the heated solution is naturally cooled down to a room temperature. The temperature of the solution reaches 40-20° C., it is filtered using a filter cloth or the like to remove a solid content, thereby preparing a *Portulaca oleracea* L. hot water extract in a form of a solution.

According to one embodiment of the present invention, a *Portulaca oleracea* L. solvent extract can be extracted by adding, a solvent such as ethanol, methanol, or 1,4-butylene glycol to a dried whole plant of *Portulaca oleracea* L. Preferably, 70% (v/v) ethanol is used.

According to one embodiment of the present invention, a method for producing a *Portulaca oleracea* L. fermented extract is as follows. A washed and dried whole plant of *Portulaca oleracea* L. is pulverized to produce a powder 5 to 10 times of purified water relative to dry weight of *Portulaca oleracea* l. is added to the *Portulaca oleracea* L. powder, followed by inoculation with yeast or lactic acid bacteria, and cultivation for 1-15 days, preferably 1-7 days, more preferably 2-4 days at 30-36° C., thereby producing a fermented extract. Yeast or lactic acid bacteria can be inoculated at a rate of $1 \times 10^4$ to $1 \times 10^5$ cells per liter of culture solution at the time of fermentation and cultured under a normal condition or an aerobic or anaerobic condition depending on the property of microorganism.

In the present invention, a red *Ginseng* can be produced by a known method, or a commercially available product can be used. Specifically, 3-4 year old fresh *Ginseng* is washed, steamed at 90 to 100° C., dried, and aged for 6 months to 1 year. 5 to 10 times of purified water relative to dry weight of red *Ginseng* is added to the red *Ginseng*, and is extracted by adding ethanol and then concentrated to prepare a red *Ginseng* solution. For convenience of use in the present invention, a red *Ginseng* in liquid form is used in the present invention.

The natural shampoo composition of the present invention may further comprise at least one of substance selected from the group consisting of polyquaternium, disodium laureth sulfosuccinate (LES), cocamide diethanol amine (CDA), cocobetaine, olive liquid, silk amino acid, peptide, glycerin, betaine, panthenol, provitamin F, phyto ps and essential oil. More preferably, the additional substance may include at least 10 species. The additional substance are natural surfactants and functional additives.

The polyquaternium is a thickener, which is a cationized product of natural cellulose (hydroxyethyl cellulose). Polyquaternium improves the viscosity of the composition, imparts a treatment effect, prevents hairs from being disturbed after use of the shampoo, and improves damaged hairs.

The disodium laureth sulfosuccinate (LES) is an anionic surfactant obtained by processing palm oil. The LES is less irritating to the skin and can form a rich foam, thereby imparting detergency to the composition.

The cocamide diethanol amine (CPA) is a nonionic surfactant obtained from coconut oil, and can be used as a foam stabilizer and a viscosity-forming agent.

The cocobetaine is an amphoteric surfactant obtained from coconut oil and is a hypoallergenic ingredient having a stimulus of 0-1. Since cocobetaine has the zwitterionic property, it can impart antibacterial activity, antistatic effect, and conditioning effect to the composition.

The olive liquid (olive oil PEG-7 ester) is a hypoallergenic anionic surfactant produced from an olive oil-extracted fatty acid, and has excellent detergency and can impart a skin moisturizing effect.

The silk amino acid (hydrolyzed silk, Butylene glycol) is an ingredient obtained by hydrolyzing silkworm cocoons, and it is rich in amino acids and thus supplies nourishment, to scalp and hair, and restores damaged hairs.

The peptide acts to promote a hair growth and reduce a hair loss. Preferably, a copper-tripeptide may be used in the present invention. The glycerin is used as a moisturizing agent and may maintain a moisture balance.

The betaine is used as a moisturizing agent and has a hair-damaging preventing effect and imparts gloss to hairs, The panthenol is an alcohol derivative of pantothenic acid, comprising D-panthenol, L-panthenol, DL-panthenol, and the like, but is not limited thereto. Panthenol has a calming effect on scalp, a moisturizing effect, and a hair conditioning effect.

Provitamin (tocopheryl acetate) is an antioxidant substance produced by combining a natural tocopherol (vitamin E) and acetic acid, and has an excellent moisturizing effect.

Phyto-ps is a natural preservative as a substance produced by mixing a higher alcohol (having 6 or more carbon number), moutan Radicis Cortex extract and scutellariae Radix extract and has an antioxidant effect, an anti-inflammation effect and an skin regeneration promoting effect.

The essential oil is an oil obtained by mixing ylang ylang oil and lavender oil at a weight ratio of 1:1, and has a calming effect on scalp and used as a fragrance.

According to one embodiment of the present invention, the natural shampoo composition comprises 30-50 wt % white dandelion extract solution, 1-10 wt % *Portulaca oleracea* L. extract, 1-5 wt % red *Ginseng*, 0.1-1.0 wt % polyquaternium, 20-30 wt % LES, 3-7 wt % CDA, 3-7 wt % cocobetaine, 0.1-1.0 wt % olive liquid, 3-7 wt % silk amino acid, 2-4 wt % peptide, 1-3 wt % glycerin, 0.4-2 wt % betaine 0.1-1.0 wt % panthenol, 0.1-1.0 wt % provitamin E, 0.1-1.0 wt % phyto ps, 0.1-1.0 wt % essential oil and balance water, based on the total weight of the shampoo composition.

According to one embodiment of the present invention, the shampoo composition of the present invention may further comprise a calamansi extract. The calamansi extract is obtained by adding water at 60-80° C. of 20-40 times the weight of a dry pulverized product of calamansi fruit to a dry pulverized product thereof; extra ting active ingredients for 1-5 hours; and then filtering the solution using a filter cloth to remove solids. The calamansi extract may be contained in an amount of 1-3 wt % based on the total weight of the composition.

The above mentioned natural shampoo composition can improve a condition of scalp and hairs, prevent a hair loss, and promote a hair-growth. In addition, it is excellent in preservation ability as it contains cinnamon which is a natural preservative, and also has an effect of eliminating Demodex folliculorum.

Hereinafter, the present invention will be described in detail by way of examples, but the scope of the present invention is not limited thereto.

Preparation Example 1—Preparation of White Dandelion Extract Solution 100 g of washed, dried and finely ground whole plant of white dandelion was put into 1000 g of purified water and heated to 100° C. When the solution reached 100° C., it was slowly cooled to 50° C. and 10 g of cinnamon was put into the above solution, and then heated again to 100° C. When it reached 100° C., it was slowly cooled to 40° C. The cooled solution was filtered with a filter cloth to prepare a white dandelion extract solution.

Preparation Example 2—Preparation of *Portulaca oleracea* L. Extract 100 g of washed and dried whole plant of *Portulaca oleracea* L. was prepared. 1000 g of purified water was added to the above whole plant of *Portulaca oleracea* L. and heated to 100° C. When the solution reached 100° C., it was slowly cooled to 40° C. The cooled solution was filtered with a filter cloth to prepare *Portulaca oleracea* L. extract.

Preparation Example 3—Preparation of Red *Ginseng* Extract

After washing of a 3-year-old fresh *Ginseng*, it was steamed at 90 to 100° C. for 1 hour, dried, and then aged for 6 months. Purified water of 10 times based on dry weight of red *Ginseng* was added to the aged red *Ginseng*, and ethanol was added thereto such that ethanol concentration is finally 1% (v/v) and concentrated to prepare a red *Ginseng* extract.

EXAMPLES AND COMPARATIVE EXAMPLES

A natural shampoo composition was prepared with the composition of Table 1 below. The ingredients besides Preparation examples 1 to 3 were used by purchasing from Hauyon Co., Ltd.

TABLE 1

(Unit: wt %)

| Item | Example 1 | Example 2 | Example 3 | Comp. example 1 | Comp. example 2 | Comp. example 3 | Comp. example 4 |
|---|---|---|---|---|---|---|---|
| White Dandelion Extract solution (Prep. Example 1) | 45 | 30 | 50 | — | 45 | — | — |
| *Portulaca oleracea* L. extract (Prep. Example 2) | 3 | 3 | 3 | — | — | 3 | — |
| Red ginseng extract (Prep. Example 3) | 1 | 1 | 1 | — | 1 | 1 | 1 |
| polyquaternium | 0.1 | 0.1 | 0.1 | 0.1 | 0.1 | 0.1 | 0.1 |
| LES | 20 | 20 | 20 | 20 | 20 | 20 | 20 |
| CDA | 3 | 3 | 3 | 3 | 3 | 3 | 3 |
| cocobetaine | 3 | 3 | 3 | 3 | 3 | 3 | 3 |
| olive liquid | 0.1 | 0.1 | 0.1 | 0.1 | 0.1 | 0.1 | 0.1 |
| silk amino acid | 3 | 3 | 3 | 3 | 3 | 3 | 3 |
| peptide hs | 2 | 2 | 2 | 2 | 2 | 2 | 2 |
| glycerin | 2 | 2 | 2 | 2 | 2 | 2 | 2 |
| betaine | 0.4 | 0.4 | 0.4 | 0.4 | 0.4 | 0.4 | 0.4 |
| panthenol | 0.1 | 0.1 | 0.1 | 0.1 | 0.1 | 0.1 | 0.1 |
| provitamin E | 0.1 | 0.1 | 0.1 | 0.1 | 0.1 | 0.1 | 0.1 |
| phyto ps | 0.1 | 0.1 | 0.1 | 0.1 | 0.1 | 0.1 | 0.1 |
| essential oil | 0.1 | 0.1 | 0.1 | 0.1 | 0.1 | 0.1 | 0.1 |
| purified water | balance | balance | balance | balance | balance | balance | balance |
| Total | 100 | 100 | 100 | 100 | 100 | 100 | 100 |

Experimental Example 1: Measuring of Scalp Itching-Alleviating Effect and Dandruff-Alleviating Effect For the above Examples 1 to 3 and Comparative Examples 1 to 4, scalp itching and dandruff alleviating effects were measured. 80 persons of men and women in their forties to fifties with scalp itching and dandruff were selected and divided into 8 groups of 10 persons. Each group is consisted of 5 males and 5 females. Each group was allowed to wrap their hairs once a day for 3 months using shampoo co positions of Examples 1 to 3 and Comparative Examples 1 to 4, respectively. For positive control, one group of males and females used minoxidil for 3 months in a given amount and manner. After 3 months, each group was assessed for a degree of itching mitigation, a degree of dandruff mitigation, and a feeling of stimulation in 5 levels, and the scores thereof were given in units of one point with the perfect score being five points. The average scores of each group were calculated and shown in Table 2 below.

As shown in Table 2, shampoo compositions of Examples 1 to 3, including all of a white dandelion extract solution, a *Portulaca oleracea* L. extract and a red *Ginseng*, were excellent in an itching relief effect and dandruff relief effect. In addition, they showed an excellent effect even in comparison with the case of containing either one or two kinds of white dandelion extract solution, *Portulaca oleracea* L. extract and red *Ginseng*. They also were not stimulating.

Experimental Example 2: Measurement of Hair Loss Prevention Effect and Hair Growth Effect For the above Examples 1 to 3 and Comparative Examples 1 to 4, hair loss prevention effect and hair growth effect were measured. This experiment was performed by selecting subjects with hair loss symptoms. 80 persons of men and women in their forties to fifties were selected and divided into 8 groups of 10 persons. Each group consisted of 5 males and 5 females. Each group was allowed to wrap their hairs once a day for 3 months using shampoo compositions of Examples 1 to 3 and Comparative Examples 1 to 4,

TABLE 2

| Item | Example 1 | Example 2 | Example 3 | Comp. example 1 | Comp. example 2 | Comp. example 3 | Comp. example 4 | positive control |
|---|---|---|---|---|---|---|---|---|
| a degree of itching mitigation | 4.5 | 4.4 | 4.7 | 2.5 | 4.2 | 2.3 | 2.1 | 2.0 |
| a degree of dandruff mitigation | 4.3 | 4.2 | 4.3 | 2.6 | 4.0 | 2.5 | 2.2 | 2.0 |
| a feeling of stimulation | 1.0 | 1.0 | 1.0 | 1.0 | 1.0 | 1.0 | 1.0 | 3.0 |

1: no effect or no stimulus.
2: less effect or less stimulus.
3: normal effect or normal stimulus.
4: a little effect or a little stimulus.
5: a lot of effect or a lot of stimulus.

respectively. For positive control, one group of males and females used minoxidil for 3 months in a given amount and manner. After 3 months, each group was assessed in five levels for average daily hair loss, a determination result by the naked eye (Visual evaluation), and a degree of subjective symptom improvement at the time of hair washing and the scores thereof were given in units of one point with the perfect score being five points. The average scores of each group were calculated and shown in Table 3 below. The average score of each group was calculated and shown in Table 3 below.

TABLE 3

| Item | Example 1 | Example 2 | Example 3 | Comp. example 1 | Comp. example 2 | Comp. example 3 | Comp. example 4 | positive control |
|---|---|---|---|---|---|---|---|---|
| Visual evaluation | 4.3 | 4.0 | 4.8 | 2.1 | 3.5 | 2.7 | 2.4 | 2.6 |
| subjective symptom improvement | 4.2 | 3.9 | 4.6 | 2.3 | 3.6 | 2.6 | 2.2 | 2.5 |
| average daily hair loss | 4.3 | 3.9 | 4.6 | 2.3 | 3.8 | 2.6 | 2.4 | 2.6 |

1: worse
2: constancy
3: slightly improved
4: moderately improved
5: much improved As can be seen from the above Table 3, shampoo compositions of Examples 1 to 3 including all of a white dandelion extract solution, a *Portulaca oleracea* L. extract and a red *Ginseng*, were excellent in a hair loss prevention. In addition, they showed excellent effect even in comparison with the case of containing either one or two kinds of white dandelion extract solution, *Portulaca oleracea* L. extract and red *Ginseng*.

Experimental Example 3: Test for Feeling of Use

With respect to Example 3 and Comparative Example 1, the Feeling of Use was measured. A total of 30 persons of women aged 25-35 years were selected, and shampoo composition of Example 3 was used on the first day, and shampoos originally used by the subjects respectively were used for 7 days thereafter. On the ninth day, the shampoo composition of Comparative Example 1 was used. Test results were evaluated in five levels for bubble, shine, smoothness, touch on use, and touch after drying, and the scores thereof were given in units of 1 point with the perfect score being 5 points. The average scores of each group were calculated and shown in Table 4 below.

TABLE 4

| Item | Example 3 | Comp. Example 1 |
| --- | --- | --- |
| bubble | 3.8 | 3.8 |
| shine | 4.1 | 3.1 |
| smoothness | 4.3 | 3.7 |
| touch on use | 4.1 | 3.5 |
| touch after drying | 4.0 | 3.2 |

1: bad, 2: a little bad, 3: moderate, 4: a little good, 5: good

As can be seen from the above Table 4, the shampoo composition of Example 3 including all of a white dandelion extract solution, a *Portulaca oleracea* L. extract and a red *Ginseng* was excellent in Feeling of Use as a shampoo.

The invention claimed is:

1. A shampoo composition for hair loss prevention and hair growth, comprising 30-50 wt % of white dandelion extract solution, 1-10 wt % of *Portulaca oleracea* L. extract, 1-5 wt % of red *Ginseng*, 0.1-1.0 wt % of polyquaternium, 20-30 wt % of disodium laureth sulfosuccinate, 3-7 wt % of cocamide diethanol amine, 3-7 wt % of cocobetaine, 0.1-1.0 wt % of olive liquid, 3-7 wt % of silk amino acid, 2-4 wt % of peptide, 1-3 wt % of glycerin, 0.4-2 wt % of betaine, 0.1-1.0 wt % of panthenol, 0.1-1.0 wt % of provitamin E, 0.1-1.0 wt % of phyto PS, and 0.1-1.0 wt % of essential oil as active ingredients, and balance water, based on a total weight of the shampoo composition, wherein phyto PS is a preservative comprising a higher alcohol having 6 or more carbon atoms, Moutan Radicis Cortex extract and Scutellariae Radix extract.

2. The shampoo composition according to claim 1, wherein the white dandelion extract solution is a hot water extract of white dandelion and cinnamon obtained by heating a mixed solution of white dandelion and water to 80-100° C.; then cooling the mixed solution to 60-40° C.; adding cinnamon to the cooled mixed solution and heating again the mixed solution to 80-100° C.; and then again cooling the heated solution.

* * * * *